United States Patent [19]
Levy

[11] Patent Number: 6,054,099
[45] Date of Patent: *Apr. 25, 2000

[54] URINE SPECIMEN CONTAINER

[76] Inventor: Abner Levy, 325 N. Oakhurst Dr., P4, Beverly Hills, Calif. 90210

[ * ] Notice: This patent issued on a continued prosecution application filed under 37 CFR 1.53(d), and is subject to the twenty year patent term provisions of 35 U.S.C. 154(a)(2).

[21] Appl. No.: 08/647,526

[22] Filed: May 15, 1996

[51] Int. Cl.[7] ................................................. B01L 3/00
[52] U.S. Cl. .......................... 422/102; 422/99; 422/100; 436/180; 600/573; 600/577; 215/235; 215/237; 215/296; 215/297; 215/349; 215/350
[58] Field of Search .............................. 422/99, 100, 101, 422/102, 103; 436/180; 128/760, 761, 771; 215/247, 249, 296, 297, 298, 299, 303, 305, 349, 350, 235, 237, 238, 232; 600/573, 577

[56] References Cited

U.S. PATENT DOCUMENTS

| | | | |
|---|---|---|---|
| 3,424,329 | 1/1969 | Hershberg et al. | 215/247 |
| 3,629,873 | 12/1971 | Long | 4/220 |
| 3,676,076 | 7/1972 | Grady | 422/100 |
| 4,040,791 | 8/1977 | Kuntz | 422/102 |
| 4,042,337 | 8/1977 | Griffith | 422/102 |
| 4,064,760 | 12/1977 | Benjamin | 73/863.52 |
| 4,248,355 | 2/1981 | Kolb et al. | 422/102 X |
| 5,016,771 | 5/1991 | Finneran | 215/247 X |
| 5,088,612 | 2/1992 | Storar et al. | 215/247 |
| 5,270,211 | 12/1993 | Kelln et al. | 436/43 |
| 5,352,413 | 10/1994 | Kratzer et al. | 422/102 X |
| 5,395,590 | 3/1995 | Swaniger et al. | 422/102 X |
| 5,443,791 | 8/1995 | Cathcart et al. | 422/65 |
| 5,449,071 | 9/1995 | Levy | 206/569 |
| 5,511,557 | 4/1996 | Hazard et al. | 600/573 |
| 5,753,186 | 5/1998 | Hanley et al. | 422/101 |
| 5,904,677 | 5/1999 | Drummey et al. | 604/415 |

OTHER PUBLICATIONS

The Fisher 88 Catalog, 1987, pp. 1162–1163.

*Primary Examiner*—Maureen M. Wallenhorst
*Attorney, Agent, or Firm*—Natan Epstein; Beehler & Pavitt

[57] ABSTRACT

A container for liquid medical specimens such as urine specimens includes a container with a wide mouth opening for facilitating deposition of a urine sample, a removable cap for closing the mouth opening and an impermeable sheet liner under the cap for making a fluid tight seal with the rim. The liner is rupturable with the blunt tip of a laboratory pipette inserted through a small hole in the cap for drawing a sample of a urine specimen without removing the cap of the container. The hole in the cap may remain open after collection of a urine specimen in the container, as leakage is prevented by the liner. Alternatively, a small secondary cap may close the hole in the main cap. An optional decanter may be inserted through the hole in the cap for piercing the liner to facilitate pouring of the contents without removing the cap. A method of using the novel container for conveying a liquid medical specimen from a specimen collection site to a geographically removed laboratory site is disclosed.

21 Claims, 2 Drawing Sheets

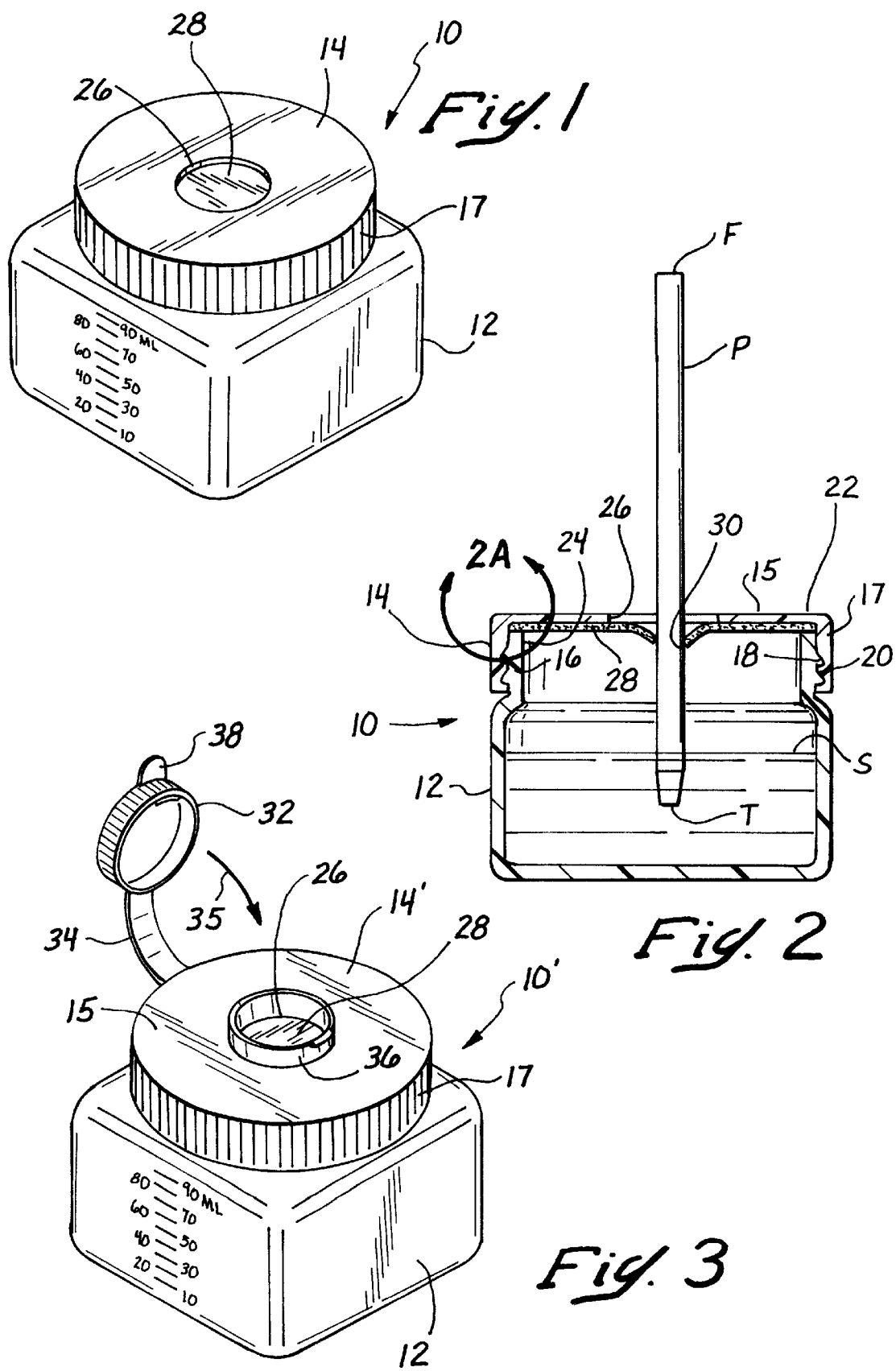

URINE SPECIMEN CONTAINER

BACKGROUND OF THE INVENTION

1. Field of the Invention

This invention relates to containers primarily used for collection and transport of urine specimens from a specimen collection site to a clinical laboratory for analysis and possible subsequent storage.

2. State of the Prior Art

Urine specimens are routinely taken from individuals by medical personnel for laboratory analysis. The analysis may be for purposes of diagnosing disease, or for detecting the use of a controlled substance by the donor. The specimens are collected at a location, typically a medical doctor's office or hospital, from where the specimen must be transported to a clinical laboratory site where the specimen is subjected to the desired analysis. The urine sample is usually collected and shipped in the same container. The laboratory site may be quite distant from the collection site and the specimen container is often forwarded by mail including air mail. It is necessary that the specimen be leak proof during handling in transport, even when subjected to reduced atmospheric pressure as may occur during air transport.

Existing containers used for collection and transport of urine specimens suffer from a number of shortcomings.

Conventionally, vials and containers of various designs having threaded, twist-off closures or caps have been used for this purpose. While such containers perform their intended function, laboratory personnel handling hundreds of such containers per day can develop repetitive motion syndromes and consequent disability due to the repeated wrist motion required to open and close the twist-off caps. Secondly, the urine specimen is usually collected by the patient who urinates directly into the open container, and then closes the twist-off cap. The amount of urine needed for most laboratory analyses is not large, and the containers used for collection of the specimens are accordingly rather small. In particular, the mouth opening of the container is typically smaller than 50 millimeters. Collection of a specimen into such an opening does not pose a particular problem for male patients, but is difficult for female patients. Thirdly, the liquid contents of small, wide mouth containers have a tendency to spill over or splash out of the container during handling and particularly during removal of the twist-off cap of such a container.

A need exists for improved containers for medical specimens which are secure against leakage yet more easily handled by both patients and laboratory personnel to facilitate specimen collection, reduce the chances of spillage, and alleviate the repetitive motion hazard posed by existing designs.

SUMMARY OF THE INVENTION

These and other shortcomings of the prior art are addressed by the present invention, which provides a specimen container assembly having a container with a mouth opening of relatively large diameter defined by a rim on a container neck, and a twist-off cap for closing the mouth opening. The cap has a hole of substantially smaller diameter than the relatively large diameter of the mouth opening. An impermeable liner between the twist-off cap and the rim makes a fluid tight seal when the cap is secured to the container. The liner is selected and adapted for piercing with the tip of a laboratory pipette through the hole in the cap, so that a sample of the container's contents may be drawn without removing the twist-off cap.

Preferably the liner is pressure sensitive for making an adhesive seal with the rim of the container when pressed thereagainst by the twist-off cap. In one form of the invention, a pull-off cap may be provided for closing the hole on the twist-off cap, as by engagement with a collar around the hole. The pull-off closure can be flexibly connected against separation from the twist-off cap. For example, the twist-off cap and the pull off cap may be formed as a unit with an integral connecting strap or the like, as by injection molding.

A further improvement according to this invention concerns a decanter insert, which may be generally shaped as a relatively short tube or small funnel having open upper and lower ends, and having a midportion sized to make a close fit in the hole of the twist-off cap thereby to support its upper end above the twist-off cap with its lower end extending into the container. The lower end of the insert is adapted, e.g. by tapering to a narrow diameter or a point, for piercing the liner through the hole, so that the liquid contents of the container may be dispensed by pouring through the insert without removing the twist-off cap from the container.

Optionally, the decanter insert has an insert cap for closing its upper end such that the container may be substantially sealed with the decanter fitted in the hole of the twist-off cap. The insert cap may be connected to the decanter insert and may be unitarily formed therewith. The decanter insert may have a pouring spout at its upper end to facilitate dispensation of the liquid contents. The insert may have a detent, for example located at a midportion of the insert, retentively engageable to the twist-off cap for retaining the insert against withdrawal from the hole. For example, the detent can make either a friction fit or a snap fit in the hole with the twist-off cap.

More broadly, the present invention contemplates a system for conveying liquid specimens from a collection site to a laboratory site, comprising the container with twist-off cap as described above in combination with the decanter insert. Decanter inserts may be provided in bulk quantities to clinical laboratories for use with specimen containers forwarded to them from specimen collection sites.

This invention also includes a method for conveying a liquid medical sample from a specimen collection site for analysis at a laboratory site removed. The novel method is practiced by providing a container having a mouth opening of relatively large diameter defined by a rim of the container and a twist-off cap engageable to the container for closing the opening, the twist-off cap having a hole therein of substantially smaller diameter than the diameter of the mouth opening, and a liner in the twist-off cap covering the hole and adapted to make liquid tight sealing engagement with the rim in a closed condition of the twist-off cap; depositing a liquid medical sample in the container through said mouth opening; closing the mouth opening with the twist-off cap; and conveying the container to the laboratory site from the specimen collection site. At the laboratory site the contents of the specimen container may be sampled for analysis by one of two methods.

A first approach consists in piercing through the liner with the tip of a laboratory pipette and withdrawing a sample of the specimen from the container with the pipette. The hole may be covered with a pull-off cap during transport of the specimen container to the laboratory site, and the container may be closed with the pull-off cap after withdrawal of the specimen sample for storage of a remaining portion of the specimen in the same container.

An alternate approach involves providing a decanter insert as described above, fitting the insert into the hole of the twist-off cap by pressing its lower end through the liner and into the container, and pouring out a sample of the specimen from the container through the decanter insert. The decanter insert may then be closed with a cap for storing the container with the remaining portion of the specimen.

These and other advantages, features and improvements will be better understood from the following detailed description of the preferred embodiments with reference to the accompanying drawings.

BRIEF DESCRIPTION OF THE DRAWINGS

FIG. 1 is a perspective view of a first form of the biological specimen container assembly according to this invention;

FIG. 2 is a cross-section taken in elevation of the specimen container assembly of FIG. 1, illustrating the perforation of the impermeable liner with a laboratory pipette for drawing a sample of the biological specimen from the container assembly.

FIG. 3 is a perspective view of a second form of the biological specimen container assembly provided with a pull-off cap for closing the hole in the twist-off cap.

DETAILED DESCRIPTION OF THE PREFERRED EMBODIMENTS

Figure 4:
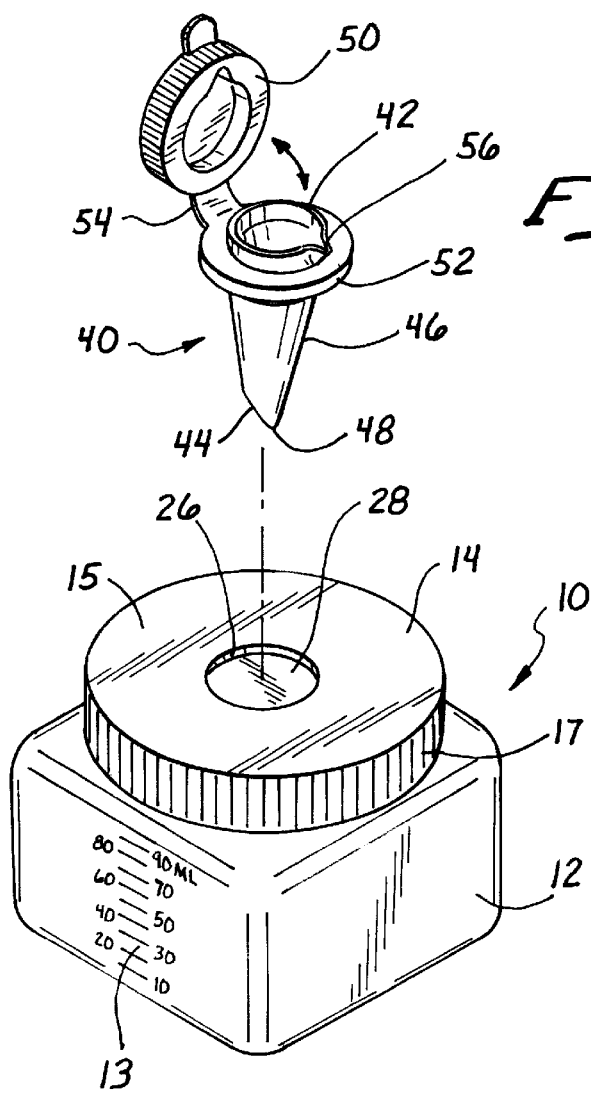
FIG. 4 is a perspective view as in FIG. 1 showing a decanter insert in position for insertion into the specimen container assembly by piercing the impermeable liner.

With reference to the accompanying drawings, FIG. 1 illustrates a urine specimen collection container assembly generally designated by the numeral 10, which is seen to include a generally rectangular container 12 and a first, twist-off cap 14. Graduations 13 may be provided on the side of the container 12. As better seen in the elevational section of FIG. 2, the twist-off cap is secured to a neck 16 of the container 12 by means of threads 18 on the cap interior mating with threads 20 on the exterior surface of the neck 16. The neck terminates at its upper end in a circular rim 22 which defines a mouth opening 24 of the container 12.

In the presently preferred form of the invention the mouth opening 24 of the container 12 has a relatively wide diameter which is equal or greater than 50 millimeters, in order to more easily accept a stream of urine from a donor of either gender. A currently preferred container 12 has a height of 1.8 inches, is 2 ⅓ inches in length along each side and 3 inches diagonally between opposite corners. The height of the neck 16 is ½ inch. It should be understood, however, that the various improvements disclosed herein are not limited to containers of any specific size or shape. In particular, the mouth opening may be smaller or larger than 50 millimeters, and the dimensions of the container 12 may be greater or smaller than specified above.

The top 15 of the twist-off cap 14 has a circular hole 26 centered in the cap and of a diameter substantially smaller than the diameter of the mouth opening 24. Preferably, the hole is circular with a diameter of approximately one-half inch. However, the size and shape of the hole 26 is not critical, provided it is sufficient to admit passage of a laboratory pipette.

A liner 28 in the cap 14 has a liner diameter closely sized to the inside diameter of the twist-off cap. The liner covers the underside of the cap 14 within the cap skirt 17, and closes the hole 26 in the cap. The liner 28 is selected to be impermeable to the liquid biological specimens to be contained in the container 12, and is covered on its exposed surface with a layer 29 of pressure sensitive adhesive. In an initial, unused condition of the container 10, the liner 28 is loosely held within the cap 14 mostly by virtue of a close fit of the circular edge of the liner within the annular skirt 17 of the cap.

Figure 2A:
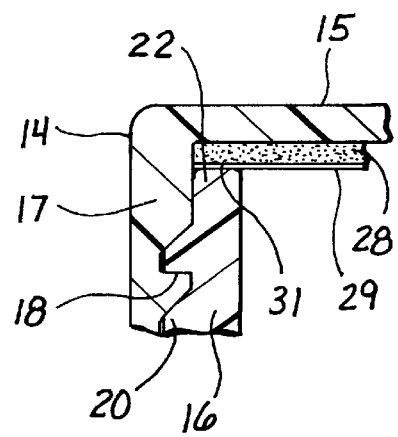
FIG. 2a is an enlarged detail taken in FIG. 2 showing the adhesive seal of the liner with the container rim.

In normal clinical usage, the container 10 is handed by medical personnel to a specimen donor, with the cap 14 either removed from the container 12 or only loosely engaged to the container neck 16 so as not to press the liner 28 to the rim 22 of the container. The donor deposits a urine sample S through opening 24 into the container 12, and then screws the cap 14 to the neck 16 of the container, tightening the cap with ordinary manual force. A narrow annular area of the adhesive layer 29 on the liner 28 is consequently pressed against the rim 22 of the container 12, as best shown in FIG. 2A. The layer 29 of pressure sensitive adhesive coating on the liner 28 is activated by the forced contact and makes an adhesive bond extending continuously about the circumference of the rim 22 of the container, forming a liquid tight seal 31 of the liner to the container 12. A presently preferred material for the pressure sensitive liner 28 is available from the 3M Company as their product number F217, a sheet material rupturable under moderate manual force, as by pressing a relatively blunt end of a typical laboratory pipette when the liner sheet is held taut across the opening of a container. The closed container assembly 10 is then forwarded, usually by commercial carrier, from the specimen collection site to the clinical laboratory where the specimen S is to be analyzed. During transport the container 12 remains sealed against leakage of the liquid specimen S by the adhesive bond 31. While the cap 14 provides mechanical support and protection for the liner 28, the liquid tight seal 31 is provided by the adhesive liner 28, so that the presence of the hole 26 in the cap is of no consequence as concerns containment of the liquid specimen S.

At the laboratory site, only a relatively small sample of the total specimen S volume is normally needed for analytical purposes. The requisite specimen sample is easily drawn by means of a conventional laboratory pipette P used as a lance to perforate the impermeable liner 28 through the hole 26 in the cap. As shown in FIG. 2, the typical pipette is a straight length of glass tubing open at top and bottom, and having a lower end which tapers in diameter to a blunt point T. This point suffices to perforate the liner 28 when pressed firmly against it through the hole opening 26 in the cap. The liner 28 is held taut across the mouth opening 24 of the container by virtue of its adhesive seal with the rim 22 of the container and also because is held captive along its circumference between the rim 22 and the cap 14 which will likely at this stage still be tightly screwed onto the container 12. The tip T of the pipette thus pierces an opening 30 in the liner 28 and passes through the hole 26 into the interior of the container 12 and is immersed in the specimen S. The top opening F of the pipette is then occluded with a finger by the laboratory technician to retain liquid in the pipette as the pipette is withdrawn from the container 10, carrying within it a sample of the biological specimen S.

The commercially available liner specified above may be generally described as a thin, substantially elastic sheet of extruded foam plastic. Such liners are widely used in the pharmaceutical industry and are known to be readily perforable or rupturable with relatively blunt ended instruments by application of moderate manual effort. Also, the specified liner is not self-sealing. That is, when perforated, punctured, broken or ruptured to pass an object of greater width than the thickness of the liner a permanent opening or hole is formed through the liner, with no significant tendency of the liner to reseal the opening.

Depending on the purpose and circumstances of the analysis, the remaining volume of the specimen S may be discarded by the laboratory together with the container 10, or the laboratory may be required to retain the specimen for a certain period of time, for example, as possible legal evidence. The container in the embodiment shown in FIGS. 1 and 2 lacks a means for conveniently closing the container once the liner 28 has been punctured, and this form of the container is best suited for use where the specimen S is to be discarded immediately after a sample has been drawn for analysis at the clinical laboratory.

FIG. 3 shows a biological specimen container 10' which is similar to that of FIG. 1 in every respect, except in that the cap 14' has been modified by provision of a pull-off cap 32 permanently attached to the cap 14' by means of a connecting strap 34. The cap 14' may be formed integrally with the pull-off cap 32 and connecting strap 34, for example, in a single cavity of an injection mold. The cap 14' also has annular collar 36 extending vertically around the center hole 26. The cap 32 seats onto the collar 36 as indicated by the arrow 35 in a friction fit to close the hole 26. The cap 32 is removed simply by lifting it up and off of the collar 36. A tab 38 is provided on the cap to facilitate this process.

The container 10' of FIG. 3 is used in the same manner as described in connection with container 10 of FIG. 1 and 2. The pull-off cap 32 will normally be in a closed condition, engaged to the twist-off cap 14' closing the hole 26 when the container 10 is handed to the specimen donor, and remains in closed condition until the container with the specimen is delivered to the clinical laboratory. At that time, the pull-off cap 32 is opened to expose the hole 26 and a sample of the specimen is drawn in the same manner as illustrated and described in connection with FIG. 2. Once the specimen sample has been drawn, the pull-off cap is closed to preserve the remaining volume of the specimen in the container 12 during storage of the container 10'.

FIG. 4 illustrates a decanter insert 40 for use with the container 10 of FIG. 1. The insert 40 is generally tubular, with an open upper end 42 and an open lower end 44. The upper end 42 is of wider aperture than the lower end and the insert has a frustoconical wall 46 tapering to a reduced diameter at the lower end 44. The lower end 44 is cut at an acute angle to the longitudinal, vertical axis of the frustoconical wall 46, as better appreciated by reference to FIG. 5, terminating in a relatively sharp point 48. The insert 40 also has an annular shoulder 52 near its upper end 42, to which is attached a decanter cap 50 by means of a flexible connecting strap 54. The upper end 42 also has a pouring spout 56 which points diametrically away from the connecting strap 54 above the shoulder 52.

The insert 40 is used at the clinical laboratory location for drawing a sample of the specimen S in the container 10. This is accomplished by pressing the sharp tip 48 of the insert through the impermeable liner 28 exposed in the hole 26 of the twist-off cap 14. The insert is pushed through the resulting hole 45 in the punctured liner until the shoulder 52 seats against the top 15 of the cap 14, a condition illustrated in FIG. 5. The diameter of the insert wall 46 just below the shoulder 52 is sized to make a close fit within the hole 26 and make a substantially leak proof sealing engagement with the cap 14, to prevent leakage of the specimen S between the insert 40 and the cap 14 through the hole 26. In a preferred form of the invention, a detent ridge 58 encompasses the wall 46 below the shoulder 52, and spaced from the shoulder so as to capture the thickness of the cap 14 between the detent 58 and shoulder 52. The detent 58 both improves the quality of the seal between the insert and the twist-off cap, and secures the insert to keep the later from accidentally falling out or being pulled out from the cap 14. The detent 58 is of slightly larger diameter than the hole 26 and makes a snap fit when the insert is pressed into the hole of the twist-off cap. The detent ridge 58 can be replaced by other suitable detent structures.

Figure 5:
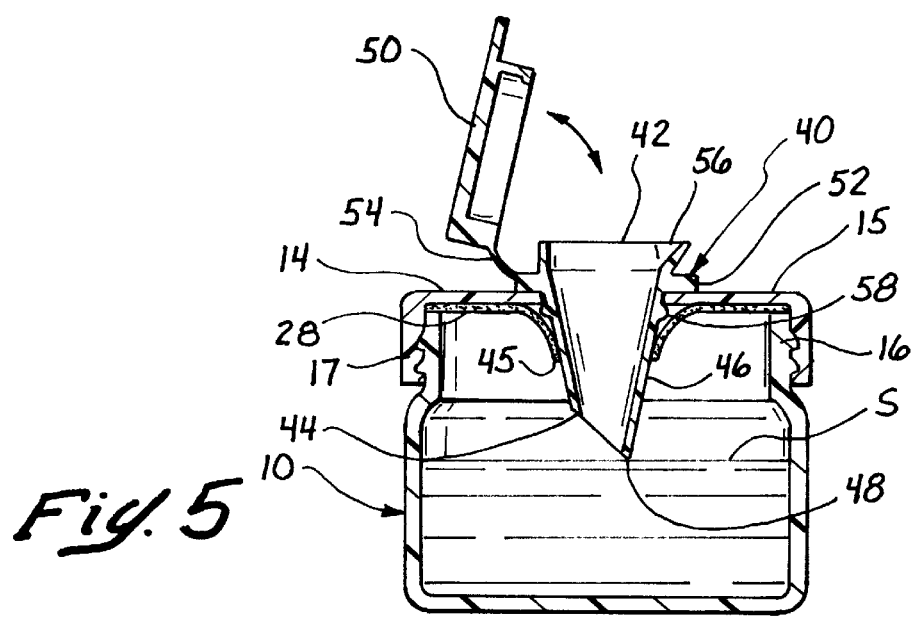
FIG. 5 is an elevational cross-section of the specimen container assembly of FIG. 4 showing the decanter insert fitted in the hole of the twist-off cap for pouring out a sample of the biological specimen.

With the decanter insert 40 in place as shown in FIG. 5, a sample of the biological specimen S can be poured out in a convenient manner by tipping the container assembly 10 with the spout 56 pointing downwardly into a second receptacle. Once the desired sample is poured, the pull-off cap 50 is pressed down onto the upper end 42 of the insert and makes a retentive fit thereon and against the shoulder 52, to close the open upper end 42 of the insert and secure the specimen content of the container 10 during a subsequent storage period.

It is contemplated that clinical laboratories will be provided with bulk quantities of decanter inserts 40, ready at hand for use with incoming container units 10 forwarded to the laboratory for analysis of the contents. The insert 40 is an alternative to use of the pipette P shown in FIG. 2. The pipette is best suited for specimens which are to be discarded after the necessary amount has been taken for immediate analysis. The insert 40 is intended for use with specimens which must be kept in storage for a period of time following the initial analysis. However, the insert 40 can be made by conventional injection molding techniques so that it can be used even with specimens which are discarded immediately after analysis, as a convenient alternative to use of the pipette.

It will be appreciated that either approach, i.e. use of the pipette P or the insert 40 for extracting a sample of the specimen S avoids the need for removal by unscrewing of the twist-off cap 14 by laboratory personnel. Such personnel are called upon to handle hundreds of such specimen containers daily, and repetitive wrist motion required to unscrew the twist-off caps of such containers have led to repetitive motion syndrome in laboratory personnel, a disabling condition. At the specimen collection site, the twist-off cap is secured by the specimen donor and normally does not require handling by medical personnel at that location.

The pull-off cap 32 in FIG. 3 and 50 in FIG. 4 are far easier to open than a twist-off cap, as they only need to pride a small distance upwardly to disengage from their closed position and will typically be lifted away by spring action inherent in their respective connecting straps 34, 54. Closure of the caps is even easier, requiring only that the cap be pressed down with light to moderate force with any part of the technician's hand. The specimen containers of this invention not only alleviate the repetitive motion hazard, but also help in speeding processing of these specimens at the laboratory, because punching through the exposed liner 28 through the hole 26 of the cap is quicker and less tiring than unscrewing and recapping the twist-off cap of the specimen container.

Another important benefit of the present invention is that the chances of spilling any part of the content of the specimen containers 10 or 10' are greatly reduced due to the fact that the wide mouth opening 24 of the container remains covered by the twist-off cap during handling in the laboratory. That is, the present invention enables the use of wider aperture specimen containers than has been practiced in the past, and at the same time greatly reduces or substantially eliminates the risk of accidental spillage of the specimen content due to the wide aperture of the container.

It should be understood that this invention is not limited to container assemblies 10 or 10' or containers 12 of any particular shape or size, and that, while certain preferred embodiments of the invention have been described and illustrated for purposes of clarity and example, many changes, substitutions, and modifications to the described embodiments will be apparent to those possessed of ordinary skill in the art without thereby departing from the scope and spirit of the present invention as defined by the following claims.

What is claimed is:

1. A specimen container assembly comprising:
    a container having a mouth opening defined by a rim, a removable cap for closing said opening, a hole in said cap of substantially smaller diameter than said mouth opening, and a relatively thin impermeable liner sheet compressed between said removable cap and said rim for making a fluid tight seal with said rim, said liner being rupturable by moderate manual effort with the relatively blunt tip of a laboratory pipette having a tip width greater than the thickness of said liner to make a permanent non-self-resealing opening in the liner at the location of the hole, whereby a sample may be drawn from said container without removing said removable cap.

2. The specimen container assembly of claim 1 wherein said liner is pressure sensitive for making an adhesive seal with said rim when pressed thereagainst by said removable cap.

3. The specimen container assembly of claim 1 further comprising a pull-off cap for closing said hole on said removable cap.

4. The specimen container assembly of claim 3 wherein said pull-off cap is flexibly connected against separation from said removable cap.

5. The specimen container assembly of claim 3 wherein said pull-off cap is adapted to engage a neck provided around said hole on said removable cap.

6. The specimen container assembly of claim 1 further comprising a decanter insert open between an upper end and a lower end thereof and having a midportion sized to make a close fit in said hole and support said upper end above said removable cap with said lower end extending into said container, said lower end being adapted for piercing said liner through said hole, such that contents of the container may be dispensed by pouring through said insert without removing said removable cap from said container.

7. The specimen container assembly of claim 6 wherein said decanter insert has a cap for closing said upper end such that said container may be substantially sealed with said decanter insert in said hole.

8. The specimen container assembly of claim 7 wherein said cap on said decanter insert is integrally connected with said decanter insert.

9. The specimen container assembly of claim 6 wherein said insert has a pouring spout at said upper end.

10. The specimen container assembly of claim 6 wherein said midportion of said decanter insert has detent means retentively engageable to said removable cap for retaining said insert against withdrawal from said hole.

11. The specimen container assembly of claim 10 wherein said detent means make a friction fit with said removable cap in said hole.

12. The specimen container assembly of claim 10 wherein said detent means make a snap fit with said removable cap in said hole.

13. The specimen container assembly of claim 6 wherein said lower end of said decanter insert tapers to a point to facilitate piercing of said liner.

14. The container assembly of claim 1 wherein said liner is a sheet supported taut across said mouth opening.

15. The container assembly of claim 1 wherein said hole remains open when said removable cap closes such that any liquid therein is contained only by said liner in said container.

16. The container assembly of claim 1 wherein said liner is held in said removable cap away from sealing engagement with said rim in an initial empty unused condition of said container, said liner being pressure sensitive for making sealing engagement with said rim responsive to tightening of said removable cap against the rim.

17. The container assembly of claim 16 wherein said liner has a pressure sensitive adhesive for making said sealing engagement.

18. A system for conveying liquid specimens from a collection site to a laboratory site, comprising: a container having a neck with a rim, a mouth opening defined by said rim, a first cap engageable to said neck for closing said mouth opening, a hole in said first cap of substantially smaller diameter than said mouth opening and a rupturable non-self-resealing relatively thin sheet liner compressed between said cap and said rim for making a liquid tight seal against said rim; and a decanter insert open between an upper end and a lower end much wider than the thickness of said sheet liner and having a midportion sized to make a close fit in said hole for supporting said upper end above said first cap with said lower end extending into said container, said lower end being adapted for piercing said liner through said hole, such that contents of the container may be dispensed by pouring through said insert without removing said first cap from said container.

19. The system of claim 18 wherein said liner is adapted for piercing with the tip of a laboratory pipette through said hole, whereby a sample may be drawn with a pipette from said container without removing said first cap.

20. The specimen container assembly of claim 18 further comprising a second cap for closing said hole on said first cap.

21. The specimen container assembly of claim 20 wherein said second cap is flexibly connected against separation from said first cap.

* * * * *